United States Patent
Keller

(10) Patent No.: US 8,070,812 B2
(45) Date of Patent: Dec. 6, 2011

(54) PROSTHESIS FOR PARTIAL REPLACEMENT OF A VERTEBRAL BODY

(75) Inventor: Arnold Keller, Kayhude (DE)

(73) Assignee: Cervitech, Inc., San Diego, CA (US)

( * ) Notice: Subject to any disclaimer, the term of this patent is extended or adjusted under 35 U.S.C. 154(b) by 0 days.

(21) Appl. No.: 11/125,313

(22) Filed: May 10, 2005

(65) Prior Publication Data

US 2006/0064167 A1     Mar. 23, 2006

(30) Foreign Application Priority Data

Sep. 23, 2004 (EP) .................................. 04022670

(51) Int. Cl.
*A61F 2/44* (2006.01)
(52) U.S. Cl. ................. 623/17.11; 623/17.15
(58) Field of Classification Search .... 623/17.11–17.16; 606/61, 246, 254–260, 264, 267, 287, 288, 606/292, 310, 313, 320, 326, 327
See application file for complete search history.

(56) References Cited

U.S. PATENT DOCUMENTS

| | | | |
|---|---|---|---|
| 4,636,217 A | | 1/1987 | Ogilvie et al. |
| 4,657,550 A | * | 4/1987 | Daher .................. 623/17.11 |
| 4,892,545 A | | 1/1990 | Day et al. |
| 4,932,975 A | | 6/1990 | Main et al. |
| 5,423,816 A | | 6/1995 | Lin |
| 5,522,899 A | * | 6/1996 | Michelson .................. 606/279 |
| 5,534,029 A | * | 7/1996 | Shima .................. 623/17.15 |
| 5,658,335 A | * | 8/1997 | Allen .................. 623/17.16 |
| 5,800,547 A | * | 9/1998 | Schafer et al. ............. 623/17.16 |
| 5,800,550 A | * | 9/1998 | Sertich .................. 623/17.16 |
| 5,895,428 A | | 4/1999 | Berry |
| 6,113,637 A | | 9/2000 | Gill et al. |
| 6,176,882 B1 | * | 1/2001 | Biedermann et al. ...... 623/17.15 |
| 6,179,873 B1 | * | 1/2001 | Zientek .................. 623/17.11 |
| 6,344,057 B1 | * | 2/2002 | Rabbe et al. ............. 623/17.11 |
| 6,375,683 B1 | * | 4/2002 | Crozet et al. ............. 623/17.15 |
| 6,432,107 B1 | | 8/2002 | Ferree |
| 6,440,169 B1 | * | 8/2002 | Elberg et al. ............. 623/17.16 |
| 6,447,546 B1 | * | 9/2002 | Bramlet et al. ........... 623/17.16 |
| 6,527,803 B1 | * | 3/2003 | Crozet et al. ............. 623/17.11 |
| 6,723,126 B1 | * | 4/2004 | Berry .................. 623/17.11 |

(Continued)

FOREIGN PATENT DOCUMENTS

DE   4109941 A1   3/1991

(Continued)

OTHER PUBLICATIONS

European Search Report dated Feb. 17, 2005, issued in counterpart foreign application.

(Continued)

*Primary Examiner* — Eduardo C Robert
*Assistant Examiner* — Lynnsy Schneider
(74) *Attorney, Agent, or Firm* — NuVasive, Inc.; Jonathan Spangler; Marjorie Jarvis

(57) ABSTRACT

A prosthesis for partial replacement of a vertebral body includes upper and lower contact plates that contact upper and lower vertebral bodies and a bridging element to be inserted into a bone cavity that bridges an intermediate vertebral body to be replaced that lies between the upper and lower vertebral bodies. This bridging element has anchoring projections which can be moved between a retracted implantation position and a protruding anchoring position.

8 Claims, 3 Drawing Sheets

U.S. PATENT DOCUMENTS

| | | | |
|---|---|---|---|
| 6,767,367 B1 * | 7/2004 | Michelson | 623/17.16 |
| 6,770,096 B2 * | 8/2004 | Bolger et al. | 623/17.16 |
| 6,808,538 B2 * | 10/2004 | Paponneau | 623/17.16 |
| 7,018,417 B2 | 3/2006 | Kuoni et al. | |
| 7,318,839 B2 * | 1/2008 | Malberg et al. | 623/17.11 |
| 2002/0128652 A1 | 9/2002 | Ferree | |
| 2002/0165613 A1 | 11/2002 | Lin et al. | |
| 2004/0049270 A1 * | 3/2004 | Gewirtz | 623/17.11 |
| 2004/0088054 A1 | 5/2004 | Berry | |
| 2004/0254644 A1 | 12/2004 | Taylor | |
| 2005/0004572 A1 * | 1/2005 | Biedermann et al. | 606/61 |
| 2005/0004671 A1 * | 1/2005 | Ross et al. | 623/17.11 |
| 2005/0004673 A1 * | 1/2005 | Kluger | 623/17.11 |

FOREIGN PATENT DOCUMENTS

| | | |
|---|---|---|
| DE | 201 15 281 U1 | 11/2001 |
| DE | 10145668 A1 * | 4/2003 |
| EP | 0 560 140 A1 | 9/1993 |
| EP | 0567424 | 10/1993 |
| EP | 0951879 A2 | 10/1999 |
| EP | 1104665 A1 | 6/2001 |
| EP | 1188424 A1 * | 3/2002 |
| EP | 1290993 | 3/2003 |
| EP | 1417940 | 5/2004 |
| FR | 2846876 | 5/2004 |
| WO | WO-01/03614 | 1/2001 |
| WO | WO-2004/080356 | 9/2004 |

OTHER PUBLICATIONS

Keller, U.S. Office Action mailed Jul. 7, 2009, directed to U.S. Appl. No. 11/137,707; 6 pages.

Keller, U.S. Office Action mailed Dec. 26, 2008, directed to U.S. Appl. No. 11/137,707; 7 pages.

Keller, U.S. Office Action mailed Sep. 21, 2007, directed to U.S. Appl. No. 11/137,707; 7 pages.

Keller, U.S. Office Action mailed Feb. 23, 2007, directed to U.S. Appl. No. 11/137,707; 6 pages.

* cited by examiner

Fig. 1
Fig. 2
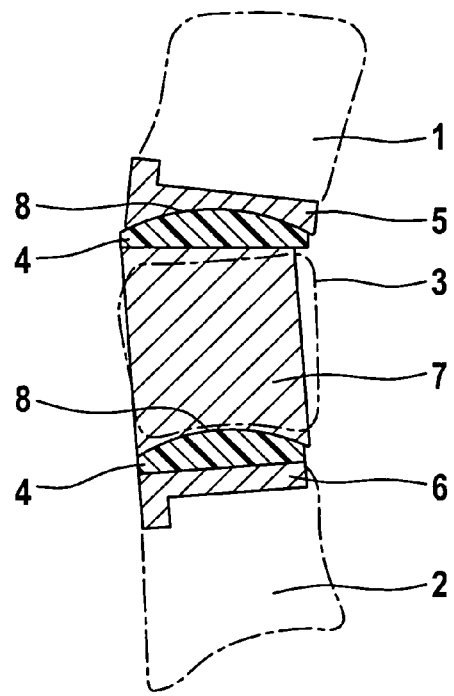
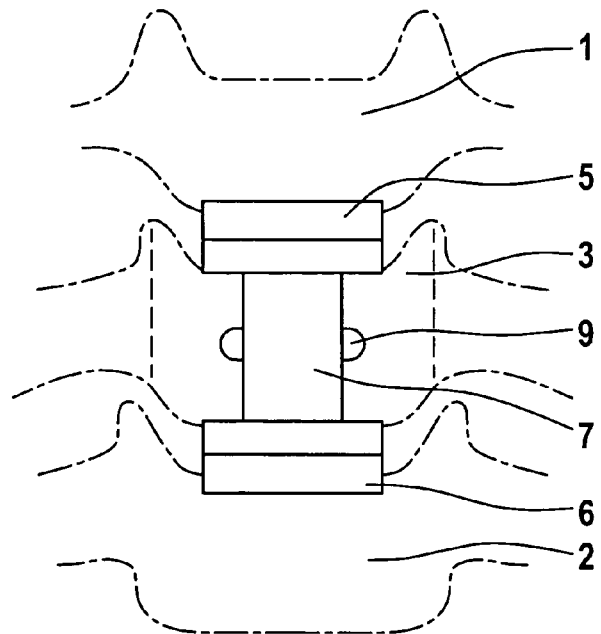

PROSTHESIS FOR PARTIAL REPLACEMENT OF A VERTEBRAL BODY

FIELD AND BACKGROUND OF THE INVENTION

If a vertebral body is so severely damaged through disease or injury that it can no longer satisfy its supporting function between the two adjacent vertebral bodies, it can be partially replaced by a known prosthesis (DE-A-4109941, FIG. 8). This prosthesis comprises an upper contact plate for connection to the upper adjacent vertebral body, a lower contact plate for connection to the lower adjacent vertebral body, and, between them, a bridging part which bridges the vertebral body that is to be partially replaced. If the vertebral body to be partially replaced is completely preserved only on the vertebral arch side, a bone cavity is created on its front face and the bridging part is inserted into said bone cavity. For firm connection to the vertebral body to be partially replaced, the bridging part has laterally protruding webs which contain an oblong hole for receiving a securing screw. The securing of the prosthesis on the vertebral body to be partially replaced determines, in addition to the facet articulations, the position of said vertebral body with respect to the adjacent vertebral bodies. Only when its front faces, intended for the securing webs to bear on, are worked in such a way that the vertebra, after connection to the webs, can maintain its natural position defined by the facet articulations, is there any prospect of the prosthesis fitting so exactly that the facet articulations match in exactly the natural manner and no pain caused by movement arises. Such precise working is difficult to achieve in the confined operating site, especially as the position of the prosthesis is influenced not only by the surfaces of the bone cavity, but also by the front face and the screw holes. Inaccuracies in the production of each of these surfaces impair the exactness of the prosthesis position and may therefore lead to pain caused by movement.

SUMMARY OF THE INVENTION

A prosthesis for partial replacement of a vertebral body is known (U.S. Pat. No. 4,892,545) whose bridging part is anchored only on the two vertebral bodies adjacent to the vertebral body to be partially replaced, and which for this purpose has projections which are driven upward and downward into the adjacent vertebral bodies after the prosthesis has been inserted. These are intended to be immobilized in relation to the bridged vertebral body. No hinge is present. Since there is therefore no movement between adjacent vertebral bodies, there is also no fear of pain caused by movement resulting from imprecise positioning of the prosthesis. This known prosthesis could not therefore teach the skilled person that, by using retractable and advanceable anchoring projections arranged at another location, pain caused by movement could be avoided in prostheses equipped with a hinge.

Mechanisms for moving the anchoring projections are known or have been the subject of previous applications (EP-A-951879, EP-A-1104665, U.S. Pat. No. 4,636,217, U.S. Pat. No. 5,658,335, US-A-2002/0165613, US-A-2004/0088054, WO2004/080356). The drive means can be configured in such a way that, by being turned, it can bring about the movement of the anchoring projections. It can, for example, be configured as an eccentric cam or as a rotary cam which, in the position of rotation corresponding to the implantation position of the projections, protrudes less far toward the projections than it does in the position of rotation corresponding to the anchoring position. A particularly advantageous embodiment of the drive means is a pinion which meshes in toothed racks connected to the anchoring projections. This has the advantage that the travel covered by the projections between the implantation position and the anchoring position is not limited to the cam height of the drive means.

The object of the invention is to make available a prosthesis of the aforementioned type in which the probability of pain caused by movement is reduced.

The solution according to the invention lies in the invention as broadly disclosed and preferably in accordance with the detailed embodiments disclosed below. Accordingly, the bridging part of the prosthesis to be inserted into the bone cavity has lateral anchoring projections which can be moved between a retracted implantation position and a protruding anchoring position. This affords the possibility of first accurately placing the prosthesis, if appropriate under X-ray control, and then fixing it in its instantaneous position by simply pushing the anchoring projections out. Apart from the shaping of the bone cavity, no working steps are needed whose tolerances could have a negative effect on the exact positioning.

The bridging part should have a shape which corresponds approximately to the shape of the cavity, so that it can be inserted deep into the bone cavity and so that the anchoring projections become effective at a location where there is sufficient surrounding bone substance for solid anchoring. It preferably has a shape tapering in the direction of insertion and free from undercuts, so that the bone cavity can be produced with the greatest possible correspondence of shape. Such shapes are preferred which can be produced as easily and as precisely as possible in the bone. An example of this is a shape which is delimited by plane surfaces and which can be generated by means of a bone saw and, if appropriate, a gauge which guides said bone saw.

The shape of the bone cavity and the corresponding shape of the bridging part to be inserted determine the direction in which the inserted part could escape if it were not anchored, namely counter to the direction of insertion. Since the projections are intended to prevent movement in this direction, they must engage in the bone substance transversely with respect to this direction. This generally supposes that they are arranged laterally on the bridging part.

Since the anchoring projections are retracted during implantation, they do not impede the implantation. It is only thereafter that they are moved into the protruding anchoring position.

The anchoring projections can preferably be moved by the same mechanism. This facilitates the operation because only a single movement step is necessary to bring all jointly movable anchoring projections into the anchoring position. For this purpose, a drive means can be provided which acts on all the associated anchoring projections. It is particularly advantageous if this means displaces the anchoring projections in different directions, for example displaces two anchoring projections in opposite directions.

The anchoring projections and the drive means used to move them can expediently be actuated from that face of the implant from which the implant is inserted into the bone cavity.

So that the anchoring of the implant in the bone takes place not just by way of the anchoring projections, the part to be inserted into the bone cavity is expediently configured such that the bone tissue can connect intimately with its surface. It preferably also has openings or pores far receiving bone tissue. A hollow space can be provided which is accessible via the openings or pores and which is or can be provided with a filling of bone material (including bone replacement material).

For partial replacement of a vertebral body, a bone cavity is formed in the latter from the direction of the front face, this bone cavity matching the shape of the bridging part and receiving the latter almost completely. To ensure that this is possible, the bridging part is made narrower than the vertebral body. The bridging part and the vertebral body preferably support one another support one another via a form fit. The bridging part contains the lateral anchoring projections which hold it securely in the bone cavity.

While the projections are in their retracted implantation position, the bridging part can be inserted easily into the bone cavity. They are then pushed out, penetrate on both sides into the bone tissue and in so doing reach their anchoring position. They can expediently be actuated from the front face of the bridging part.

The invention has particular advantages when applied in the cervical vertebral column.

BRIEF DESCRIPTION OF THE DRAWINGS

The invention is explained in more detail below with reference to the illustrative embodiments depicted in the drawing, in which:

FIG. 1 shows a longitudinal section through a first illustrative embodiment in the median plane, FIG. 2 shows a front view of the same implant.

DETAILED DESCRIPTION OF THE INVENTION

Figure 3:
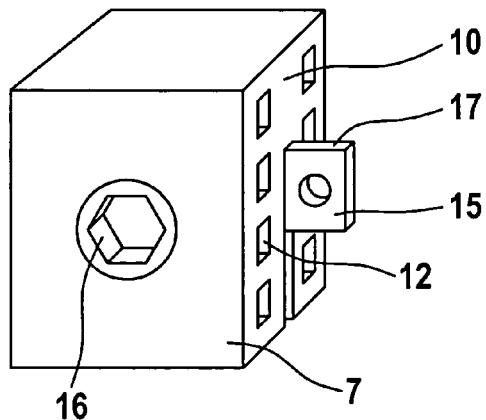
FIG. 3 shows the perspective view of a second illustrative embodiment obliquely from the front.

The illustrative embodiments concern a prosthesis for partial replacement of a vertebral body. FIG. 2 shows an upper vertebral body 1 and a lower vertebral body 2, and between them a vertebral body 3 which is to be partially replaced. A prosthesis is inserted between the upper and lower vertebral bodies. This prosthesis comprises an upper contact plate 5 connected to the upper vertebral body 1, a lower contact plate 6 connected to the lower vertebral body 2, and a bridging part 7 which connects the plates 5 and 6. Located between the contact plates 5 and 6 and the bridging part 7 there is in each case a hinge (for example according to EP-A-560140) with a hinge surface 8. This is formed, in the upper hinge, on the one hand by the bottom face of the contact plate 5 and on the other hand by a hinge part 4 connected to the bridging part 7 in a manner not shown. In the lower hinge, it is formed on the one hand by the bottom face of the bridging part 7 and on the other hand by the hinge part 4, which is connected to the lower contact plate 6 in a manner not shown. Instead of a hinge with a spherical hinge surface, another hinge type can also be used, for example one with a flexible cushion (DE-U-20115281) or with a spiral spring (DE-A-4109941). Finally, it is possible to use just one hinge between the upper contact plate 5 and the bridging part 7, or between the lower contact plate 6 and the bridging part 7.

While the contact plates 5 and 6 have a customary size which is dimensioned in the interest of low pressure forces between the contact plates and the associated vertebral bodies, the bridging part 7 has a width which is considerably smaller than that of the vertebral body 3 which is to be partially replaced. This affords the possibility of inserting the bridging part into a bone cavity which has been worked into the vertebral body 3 from the front face. Within the meaning of the claims, the bridging part represents the part which is to be inserted into the bone cavity. The bone cavity has a configuration which corresponds as exactly as possible to the configuration of the bridging part 7. This makes it possible for the implant surface to bear against the artificially created surface of the bone across as large an area as possible, and without play. On the one hand, this provides a mutual support which is substantially free from play. On the other hand, it affords the possibility of bone growth creating a stable connection between the bone and the implant. Finally, this ensures that the anchoring projections 9 provided on the implant engage in the bone tissue along substantially their full length in order to be able to transmit the anchoring forces.

The expression bone cavity is not intended to entail any restriction whatsoever in terms of shape. This applies in particular to the depth and lateral boundaries of the bone cavity. It need only be so deep that, in addition to the inserted part, there is enough lateral space to accommodate a quantity of bone material sufficient for the anchoring by means of the anchoring projections. In the example discussed here, the cavity is open at the top and at the bottom. In addition to the anchoring projections, openings 12 or pores can be provided into which bone substance can grow and anchor itself. To accelerate this process, the openings can be filled from the start with bone chips. It is also possible to coat the implant with osteoconductive or osteoinductive substance.

Figure 4:
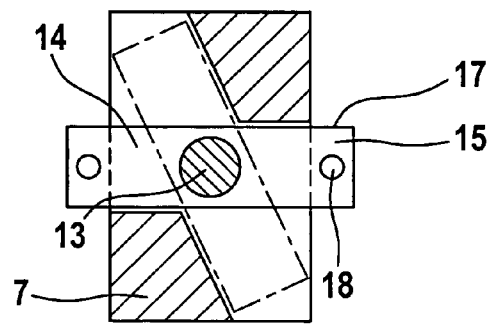
FIG. 4 shows a sectional view of the illustrative embodiment from FIG. 3.

FIGS. 3 and 4 show an illustrative embodiment with projections 15 which are retracted into the bridging part during implantation and which are then moved into the anchoring position. The bridging part 7 has a transverse slit, which appears as an non-crosshatched area in FIG. 4. A bolt 14 is mounted therein on a shaft 13, which bolt 14, in a first position of rotation indicated by broken lines, is retracted fully into the implant and, in the position of rotation indicated by solid lines, extends with its ends forming the projections 15 beyond the side surfaces 10 of the implant. The bolt 14, connected in a rotationally fixed manner to the shaft 13, is rotated into this anchoring position, with the aid of wrench attachment surfaces 16 at the front end of the shaft 13, only when the bridging part has reached the intended implantation position. During this movement, the ends 15 of the bolt 14 cut into the bone substance of the vertebra which is to be partially replaced and, in order to facilitate this procedure, they can be provided with a self-cutting configuration on the leading edge 17. In the example shown, the bolt ends 15 comprise an opening 18 into which bone substance grows and thus prevents the bolt 14 from moving back.

An important advantage of the projections, which can be driven outward after insertion of the bridging part, is that they permit subsequent correction of the position of the bridging part. If the working of the bone cavity were not to be as precise as is desirable, the projections afford the possibility of inserting the bridging part with play and leaving the exact positioning to the projections, which are then driven outward once the bridging part has reached its anatomically correct position.

The implant can contain several slits arranged in parallel and at a distance one behind the other, with bolts 14 arranged therein on the shaft 13, which bolts 14 are moved jointly into the locking state by the movement of the shaft 13 and then engage in the bone substance at a suitable axial distance behind one another.

Figure 5:
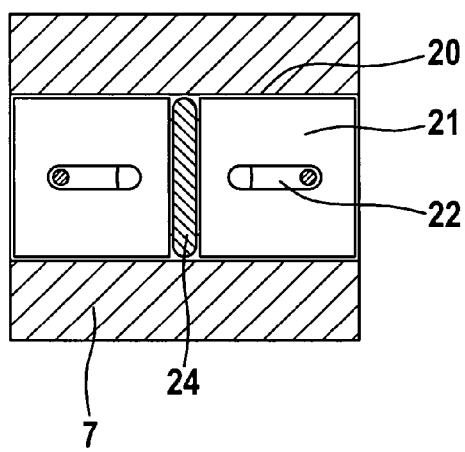
FIG. 5 shows a section through a third illustrative embodiment.
Figure 6:
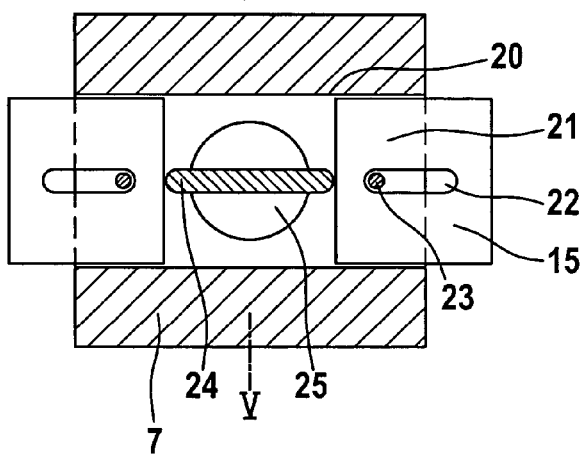
FIG. 6 shows the section according to FIG. 5 in another function position.
Figure 7:
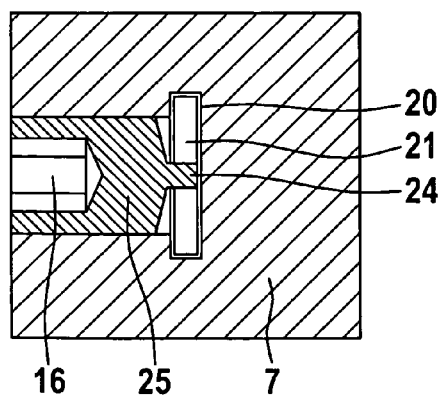
FIG. 7 shows a section along sectional line V in FIG. 6.

A further illustrative embodiment of movable anchoring projections is shown in FIGS. 5 to 7. A transverse slit 20 is provided in the bridging part 7 and serves as a guide for two bolts 21 which can assume, in said slit, the end positions shown in FIGS. 5 and 6. The ends of the bolts form the anchoring projections 15. They contain an oblong hole 22 which extends in the direction of displacement and which is traversed by a pin 23 fixed in the bridging part. This pin 23 ensures that they cannot migrate out from the implant any farther than the anchoring position shown in FIG. 6.

For transferring the bolts 21 from the implantation position according to FIG. 5 into the anchoring position according to FIG. 6, a spreading member is used which, in this illustrative embodiment, is designed as a rotary cam 24 arranged fixedly at the end of a shaft 25. If, from the position in FIG. 5 in which it lies in a narrow configuration between the bolts 21, it is turned through 90° to the position in FIG. 6, it spreads the bolts 21 away from one another until their ends protrude as anchoring projections beyond the implant and anchor the latter in the bone. At its end accessible from the front face of the bridging part, the shaft 25 is provided with wrench attachment surfaces 16 for a turning instrument. Means (not shown) can be provided which hold the shaft 25 firmly in the bridging part 7 and secure it in the anchoring position according to FIG. 6.

Figure 10:
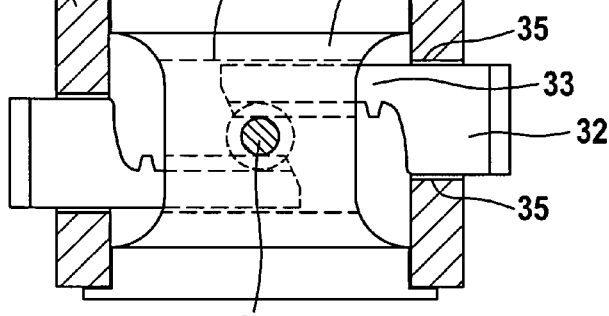
FIG. 10 shows a plan view.

FIG. 10 shows the structure of the bridging part 7 in the fourth illustrative embodiment. It is made up of a narrow core part 29 and a cage 30 which encloses the core part 29 at a distance. Secured on the top face of the core part 29 is the hinge part 4 (see FIG. 1) which, with a contact plate 5 (not shown), forms an upper hinge. On its bottom face, a hinge surface 8 is provided which, with a hinge part 4 (not shown) and a lower contact plate 6, forms a lower hinge (not shown). The cage contains a large number of holes 31 which permit ingrowth of bone substance. If so desired, this can be promoted by filling the space between the core part 29 and the cage 30 with neutral or homologous bone substance or with a bone replacement substance. This filling can be manufactured in advance.

Figure 9:
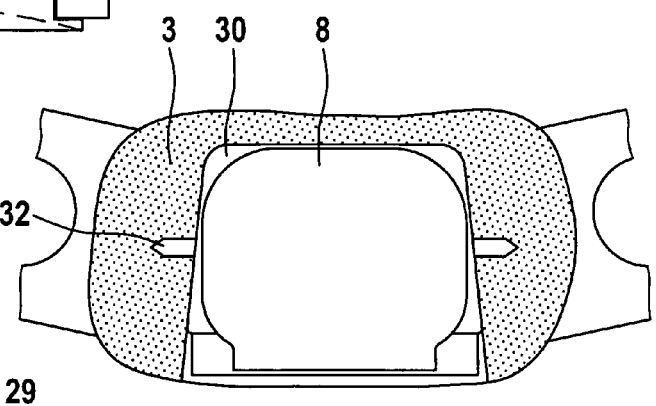
FIG. 9 shows a frontal section.

As can be seen from FIG. 9, the cage 30 is narrower than the vertebral body 3 which is to be partially replaced, so that it can be inserted into a forwardly open bone cavity formed in said vertebral body 3. Its cross-sectional shape is delimited by plane surfaces. This makes it easier to produce a bone cavity matching the shape of the cage and facilitates exact insertion of the cage.

Figure 8:
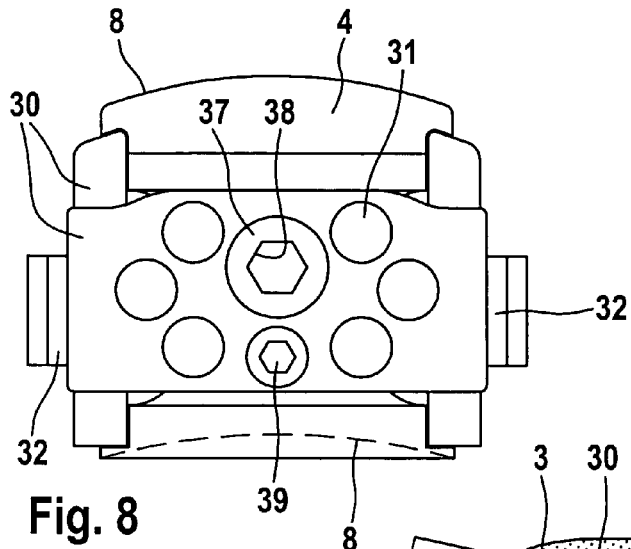
FIG. 8 shows a front view of a fourth illustrative embodiment.
Figure 11:
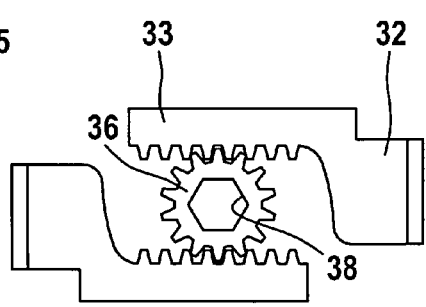
FIG. 11 shows a construction detail.

Projections 32, sharpened at the end, protrude from the side faces of the bridging part 7. In addition to the anchoring position shown in FIGS. 8 and 9, they are able to assume an implantation position (not shown) in which they are retracted into the bridging part 7. Their movement from one position to the other is effected with the aid of the mechanism shown in FIG. 11. This mechanism includes a pinion 36 as spreading element. Its teeth mesh with the teeth of toothed racks 33 which are arranged on both sides of the pinion and are connected fixedly to the anchoring projections 32. The toothed racks 33 and/or the projections 32 are mounted displaceably in their longitudinal direction in guide surfaces 34 of the core part 29 and/or guide surfaces 35 of the cage 30. The pinion 36 or the pinion shaft 37 is provided with actuating surfaces 38 which are accessible to a turning instrument from the front face of the implant. When the pinion is turned clockwise (as seen in FIG. 11), the toothed racks 33 with the projections 32 are pushed outward from the implantation position into the anchoring position. This is done once the implant has been inserted and has reached its intended position. The projections then penetrate into the bone areas located at the sides of the bone cavity and in so doing anchor the bridging part 7 therein.

To ensure that the projections do not inadvertently retract from the anchoring position during use of the prosthesis, a securing device is provided. This is designed as a securing screw 38 which, as soon as the projections have reached the anchoring position, can be screwed into a securing position in the core part 29 in order to prevent the movement of the toothed racks. For example, it can press against a toothed rack or against the pinion so as to prevent these from moving by means of friction, or it can engage in a space between the pinion 36 and a projection 32, or between the meshing teeth of pinion 36 and toothed rack 33, in order in this way to lock them positively in the anchoring position.

Figure 12:
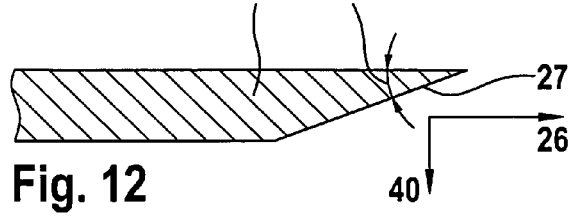
FIG. 12 shows the outer end of an anchoring projection.

According to FIG. 12, the outer end of an anchoring projection 15 or 32 is provided with a surface 27 which is inclined relative to the direction 26 in which the anchoring projection is pushed out of the implant into the anchoring position. It is therefore designated as a beveled surface. During the pushing-out movement, the surrounding bone substance subjects this beveled surface to a force component in the direction of arrow 40 transverse to the direction 26 in which the anchoring projection is pushed out. This force component is taken up by the implant, as a result of which the implant is pressed in the direction of this force. This can be exploited so that the part to be received by the bone cavity is driven farther into the bone cavity, in order to achieve the most secure fit possible.

A condition for this action of the beveled surface is that there is no identical beveled surface acting in the opposite direction on the opposite side of the anchoring projection. In the example in FIG. 9, in which the anchoring projection forms two identical cutting facets acting in opposite directions, the forces generated by these facets balance each other. In contrast to this, the beveled surface according to the invention is thus distinguished by the feature that it is arranged on one side. This applies not only to cases where there is no beveled surface present at all on the opposite side, but also to cases where an opposite beveled surface generates a lesser force component, for example because it is smaller or its angle is less favorable.

In the example according to FIG. 12, the beveled surface 27 forms a cutting facet. However, this is not a precondition for its action. For example, a blade-shaped anchoring projection could instead be guided in its entirety obliquely with respect to the direction of its blade surface.

The invention claimed is:

1. A method for partial replacement of a vertebral body comprising:
   (a) forming an implant recess within a human spine for receiving an implant, the implant recess defined by a first disc space, a second disc space, and a partial corpectomy formed in a vertebral body extending between the first disc space and the second disc space;
   (b) introducing an implant into the implant recess, the implant including a first contact plate to be positioned within the first disc space for connection to a first vertebral body, a second contact plate to be positioned within the second disc space for connection to a second vertebral body, a bridging part connecting the first and second contact plates to be positioned within the partial corpectomy extending between the first disc space and second disc space, the bridging part including at least one of a first hinge formed between a bottom of the first contact plate and a first hinge surface of the bridging part and a second hinge formed between a top of the second contact plate and a second hinge surface of the bridging part, that permits movement after implantation of the implant of the first contact plate or the second contact plate relative to the bridging part, an actuating device located on an anterior face of the bridging part, and deployable anchoring projections disposed within the bridging part; and (c) selectively deploying the anchoring projections in opposite lateral directions to penetrate into bone areas surrounding the partial corpectomy of the implant recess by rotating the actuating device.

2. The method of claim 1, wherein the bridging part is coated with at least one of an osteoconductive and osteoinductive substance.

3. The method of claim 1, wherein the bridging part has openings for receiving bone tissue.

4. The method of claim 3, further comprising:
anchoring the bridging part by allowing at least one of bone growth to the bridging part and bone growth into the openings in the bridging part.

5. The method of claim 1, wherein the first hinge and the second hinge permit movement after implantation of the implant between the first contact plate and the second contact plate relative to the bridging part.

6. The method of claim 1, wherein the bridging part has lateral side surfaces, relative to an implanted position, which are planar.

7. The method of claim 6, wherein the lateral side surfaces of the bridging part angle towards one another in a posterior direction relative to the implanted position.

8. The method of claim 1, wherein the anchoring projections have a beveled surface on an outer end of the anchoring projection such that when the anchoring projections are selectively deployed, a force is applied to the anchoring projection to secure the bridging part farther into the implant recess.

* * * * *